(12) United States Patent
Carney et al.

(10) Patent No.: US 9,927,410 B2
(45) Date of Patent: Mar. 27, 2018

(54) METHOD AND SYSTEM FOR DETECTING URINE AND/OR FECES

(71) Applicant: SCA Hygiene Products AB, Göteborg (SE)

(72) Inventors: Joshua Carney, Göteborg (SE); Pär Johansson, Hjo (SE); Anders Jönsson, Linköping (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 14/652,892

(22) PCT Filed: Dec. 21, 2012

(86) PCT No.: PCT/SE2012/051488
§ 371 (c)(1),
(2) Date: Jun. 17, 2015

(87) PCT Pub. No.: WO2014/098690
PCT Pub. Date: Jun. 26, 2014

(65) Prior Publication Data
US 2015/0330958 A1 Nov. 19, 2015

(51) Int. Cl.
*G01N 33/497* (2006.01)
*G01N 33/00* (2006.01)
(Continued)

(52) U.S. Cl.
CPC ......... *G01N 33/0001* (2013.01); *A61F 13/42* (2013.01); *G01N 33/0073* (2013.01); *G01N 33/493* (2013.01); *A61F 2013/424* (2013.01)

(58) Field of Classification Search
CPC .................................................. G01N 33/497
See application file for complete search history.

(56) References Cited

U.S. PATENT DOCUMENTS

| 5,709,222 A | 1/1998 | Davallou |
| 7,642,396 B2 | 1/2010 | Ales, III et al. |

(Continued)

FOREIGN PATENT DOCUMENTS

| CN | 101668499 A | 3/2010 |
| EP | 2518479 A1 | 10/2012 |

(Continued)

OTHER PUBLICATIONS

L.M. Ang et al., "Wireless Intelligent Incontinence Management System using Smart Diapers," Electrical Engineering/Electronics, Computer, Telecommunications and Information Technology, Proceedings of ECTI-CON, 2008, pp. 69-72, vol. 1.

(Continued)

*Primary Examiner* — Lisa Caputo
*Assistant Examiner* — Alex Devito
(74) *Attorney, Agent, or Firm* — Drinker Biddle & Reath LLP

(57) ABSTRACT

A method of detecting urine and/or feces is disclosed, which includes detecting the concentration of at least one gas component indicative of urine and the concentration of at least one gas component indicative of feces. The method also includes registering, for each gas component, a characteristic corresponding to the variation over time of the concentration of each gas component; comparing the registered characteristic with a predetermined characteristic for the corresponding gas component; indicating a presence of urine if the registered characteristic of at least one gas component indicative of urine generally conforms with the predetermined characteristic of the same gas component; and indicating a presence of feces if the registered characteristic of at least one gas component indicative of feces generally conforms to the predetermined characteristic of (Continued)

the same gas component. A system for detecting urine and/or feces is also disclosed.

15 Claims, 1 Drawing Sheet

(51) Int. Cl.
  *G01N 33/493* (2006.01)
  *A61F 13/42* (2006.01)

(56) References Cited

U.S. PATENT DOCUMENTS

| | | |
|---|---|---|
| 2004/0147888 A1 | 7/2004 | Huang et al. |
| 2004/0173006 A1 | 9/2004 | McCoy et al. |
| 2005/0099294 A1 | 5/2005 | Bogner et al. |
| 2007/0142799 A1 | 6/2007 | Ales et al. |
| 2007/0156456 A1* | 7/2007 | McGillin .............. G06F 19/327 705/2 |
| 2010/0072271 A1 | 3/2010 | Thorstensson |
| 2011/0095884 A1 | 4/2011 | Xu et al. |
| 2012/0072271 A1 | 3/2012 | Dessert et al. |
| 2012/0119915 A1 | 5/2012 | Clement et al. |
| 2012/0206265 A1 | 8/2012 | Solazzo et al. |
| 2012/0268278 A1 | 10/2012 | Lewis et al. |
| 2012/0310192 A1 | 12/2012 | Suzuki et al. |
| 2015/0301004 A1 | 10/2015 | Carney et al. |

FOREIGN PATENT DOCUMENTS

| | | |
|---|---|---|
| JP | 2001-314433 | 11/2001 |
| JP | 2002-107361 | 4/2002 |
| JP | 2003-270242 | 9/2003 |
| JP | 2005-315836 | 11/2005 |
| JP | 2006-206876 | 8/2006 |
| JP | 2007-167264 A | 7/2007 |
| JP | 2009-521259 | 6/2009 |
| JP | 2010-075463 | 4/2010 |
| JP | 3168620 U | 6/2011 |
| JP | 2011-130924 | 7/2011 |
| KR | 2009-0006641 U | 7/2009 |
| KR | 20090119157 A | 11/2009 |
| WO | WO 96/14813 A1 | 5/1996 |
| WO | WO 02/49561 A1 | 6/2002 |
| WO | WO-2005/039656 A1 | 5/2005 |
| WO | WO 2006/119523 A1 | 11/2006 |
| WO | WO 2007/073428 A1 | 6/2007 |
| WO | WO-2011/054045 A1 | 5/2011 |
| WO | WO 2011/078325 A1 | 6/2011 |
| WO | WO-2012/126507 A1 | 9/2012 |
| WO | WO 2013/061181 A1 | 5/2013 |

OTHER PUBLICATIONS

Supplementary European Search Report dated Jun. 23, 2016 issued in related European patent application No. EP 12 89 0310 (2 pages).
U.S. Office Action dated Aug. 4, 2016 from related (not counterpart) U.S. Appl. No. 14/653,887 including a Double Patenting Rejection on pp. 5-7 (12 pages).
English-language translation of a Japanese Office Action dated Jun. 13, 2016 issued in corresponding Japanese patent application No. 2015-549308 (3 pages).
English-language translation of a Japanese Office Action dated Aug. 28, 2016 issued in related Japanese patent application No. 2015-549309 (5 pages).
Extended European search report dated Aug. 3, 2016 issued in corresponding European patent application No. EP 12890394.5 (6 pages).
Office Action dated Jun. 3, 2017 in Colombia Patent Application No. 15168122 (12 pages) with a partial English translation (7 pages).
Office Action dated Feb. 17, 2017 in Russian Patent Application No. 2015129717/14 (5 pages) with an English translation (3 pages).
Colombian Office Action Resolución N° 80163 dated Dec. 5, 2017 issued in corresponding Colombian patent application No. 15168122 (21 pages) and its partial English-language translation thereof (10 pages).

* cited by examiner

METHOD AND SYSTEM FOR DETECTING URINE AND/OR FECES

CROSS-REFERENCE TO PRIOR APPLICATION

This application is a §371 National Stage Application of PCT International Application No. PCT/SE2012/051488 filed Dec. 21, 2012, which is incorporated herein in its entirety.

TECHNICAL FIELD

The present disclosure relates to a method of detecting urine and/or feces including detecting the concentration of at least one gas component indicative of urine and the concentration of at least one gas component indicative of feces.

The disclosure also relates to a system for detecting urine and/or feces, including a sensor unit including at least one gas sensor for detecting the concentration of a gas component indicative of urine and at least one gas sensor for detecting the concentration of a gas component indicative of feces, and a receiving unit connectable to the sensor and arranged for providing an indication of any presence or urine and/or feces based on information from said sensors.

BACKGROUND ART

Wearers of absorbent sanitary articles in the form of a diaper or an incontinence pad are often not in a state in which they may themselves change the article, or even in a state in which they realize that such an article needs changing. They are therefore dependant on caregivers in order to detect that a fecal or urinal incident has occurred and that there is a need to change their sanitary article. This is the case both for babies wearing diapers and also for adults in care homes or hospitals that are incapable of managing their own personal hygiene and changing their own diaper or incontinence pad, due to incompetence, dementia or physical handicaps. Hence, a reliable method of detecting fecal and/or urinal insults is of great need and importance.

A system for reliable detection of urine and/or feces would simplify the task of knowing when to change a diaper or an incontinence pad for a caregiver.

A system for detecting the occurrence of fecal and/or urine incontinence could similarly be used in other situations, for example in a facility such as a public washroom, in order to detect whether there is a need for cleaning said facility.

It is known that feces are often associated with pungent odors. The odors are due to a complex mixture of compounds produced by bacterial action which results in odorous gases which are emitted. Gases with strong odor which are emitted from feces include gases such as indole, skatole and mercaptans as well as hydrogen sulfide and ammonia. In particular, heavy organic compounds such as mercaptans (methyl sulfides) and hydrogen sulfide may spread widely as well as linger in a room after a fecal incident has occurred. Hydrogen gas is also associated with feces, but hydrogen gas is volatile and hence does not travel far or linger as long as the heavier gases.

Urine is associated with the odor of ammonia gas, which is due to urea breakdown.

It is previously known that gases which are associated with feces and urine may be detected in order to detect the occurrence of a fecal and/or urine insult. The patent application WO 2012/126507 A1 discloses a system for monitoring fecal incontinence by the use of a hydrogen gas sensor which is removably attached to a sanitary article such as a diaper. The system also includes a signaling device adapted to emit a signal when the level of hydrogen gas detected by the sensor is above a threshold value.

Furthermore, the U.S. Pat. No. 5,709,222 discloses a body waste detector that includes a gas sensor which is adapted to detect the presence of at least one gas associated with urine and at least one gas associated with feces over a predetermined time interval. Thereafter, the detector indicates the presence of urine and/or feces.

With reference to prior art technology, there is a need for improved systems and methods for detecting the presence of urine and/or feces. In particular, there is a need for improved systems and methods by means of which it is possible to distinguish between urinal and fecal incontinence with a high level of accuracy and which are easy to use.

SUMMARY

Consequently, it is desired to solve the above-mentioned problems and provide an improved system and method for detecting any presence of urine and/or feces with high accuracy and reliability. For example, it is desired to provide a method by means of which it is possible to distinguish between urinal and fecal incontinence with high accuracy.

An example of such a method of detecting urine and/or feces includes: detecting the concentration of at least one gas component indicative of urine and the concentration of at least one gas component indicative of feces. The method further includes: registering, for each gas component, a characteristic corresponding to the variation over time of the concentration of each gas component; comparing said registered characteristic with a predetermined characteristic for the corresponding gas component; indicating a presence of urine if the registered characteristic of at least one gas component indicative of urine generally conforms with the predetermined characteristic of the same gas component; and indicating a presence of feces if the registered characteristic of at least one gas component indicative of feces generally conforms to the predetermined characteristic of the same gas component.

The method may be used in care homes for detecting when incontinence has occurred, and what type of incontinence it is. Also, it may be used in ordinary homes for detecting fecal and/or urinal insults by infants wearing a diaper. It may also be used in public washrooms for identifying the occurrence of urinal and/or fecal contamination.

According to an embodiment, the above-mentioned predetermined characteristic varies over time and the registered characteristic is determined to conform to the predetermined characteristic if the registered characteristic follows the variation over time of the predetermined characteristic. The presence of a fecal or urinal incident is indicated if the registered characteristic generally conforms to the predetermined characteristic. Hence, it is also possible to determine if the gas is originating from passing gas or from discharge of feces as the same gas compound from the two may have different concentration characteristics following an incident.

The indication of any presence of urine and feces, respectively, may include determining whether the concentration of each gas component exceeds a predetermined threshold value during a predetermined period. As an example it may be determined that the concentration is exceeding a relatively high threshold value during a time interval directly following the incident and exceeding a further, relatively low, threshold value at a time interval following the first time interval. Such a registered characteristic may conform to a predetermined, expected characteristic of hydrogen gas following a fecal incident. Hence, the reliability of the method for determining the presence of urine and/or feces is higher than measuring the value of the gas just once.

In another aspect, the method includes determining if a derivative of the registered characteristic during a predetermined period of time generally conforms to a corresponding expected derivative of the predetermined characteristic. The derivates of the characteristics, i.e. corresponding to the concentration curves according to the embodiment, are indicative of the volatility of the gases and may thus be used to distinguish between different gases.

The derivates are not dependent on the level of gas, rather the characteristics, or properties, of the gas following an incident. Thus, the accuracy of the method is assured regardless if the concentration of gas discharge is high or low. With other methods in which the registered value is measured against a threshold value it may not be possible to detect a low discharge, representing a minor incontinence i.e. a low presence of urine or feces, if the threshold value is set too high.

The method may further include detecting the concentration of at least two gas components indicative of feces, registering a separate characteristic corresponding to the variation over time of the gas component concentration for each gas component indicative of feces, combining the registered separate characteristics, comparing the combined registered characteristics with a predetermined combination of characteristics and indicating presence of feces if the combined registered characteristics generally conforms with the predetermined combined characteristics.

If using a combination of two gases indicative of feces and/or urine, the method may also include assigning a weight value for each of the separate registered characteristics before combining the characteristics. Thereby, a more precise detection of urine and fecal incontinence is provided.

One example of two suitable gases are the non-volatile hydrogen sulfide gas and the volatile hydrogen gas. These have different characteristics and if both these characteristics are detected, then the presence of feces may be indicated. Thereby, the accuracy of the method is higher than basing the presence of feces on the detection of only one gas indicative of feces. The presence of two gases in combination also rules out the possibility that the gas is detected on the basis of a gas leak, a nearby diaper wearer, toilet etc.

In accordance with the disclosed method, it is also possible to detect at least two gas components indicative of urine, registering a separate characteristic corresponding to the variation over time of the gas component concentration for each gas component indicative of urine, combining the registered separate characteristics, comparing the combined registered characteristics with a predetermined combined characteristic and indicating presence of urine if the combined registered characteristic generally conforms with the predetermined combined characteristic.

A more precise detection is consequently more reliable. A more reliable method is valuable in environments where individuals are dependent on others to change their sanitary articles and the personnel or relatives are thus dependent on checking if the individual have had an incontinence incident. A method such as the one described enables a caregiver to easily detect if incontinence has occurred, and may thus easily decide if the sanitary article should be changed. The method described also distinguishes between the different types of insults. It is possible that the routine for a care home etc says that a diaper should only be changed if a fecal insult has occurred and not if a urinal insult has occurred. In such situations, the possibility to use a method that can reliably distinguish between the two is very helpful and thus a great advantage over other methods such as manually trusting one's nose for the occurrence of odors, or visually inspecting the inside of each diaper.

In certain embodiments, the gas component indicative of urine is ammonia gas and the gas component indicative of feces is chosen from hydrogen gas, hydrogen sulfide or an organic compound gas. Ammonia is preferred as indication of urine as ammonia is only present in urine. Hydrogen gas and hydrosulfide gas in combination is preferred as an indication of feces as the two concentration characteristics differ from each other, and are thus distinctly detected. The combination of the two characteristics is specific for feces.

The method of detecting urine and/or feces as described may also include providing a sensor unit, including gas sensors for each of the gas components, and transmitting information regarding detection of the gas components from the sensor unit to a receiver unit. The gas sensors can be arranged such that they detect the presence of gas from feces or urine. Hence, they can be arranged on the diaper, on the belt of the diaper wearer, on the bed or on the wall close to a possible source of urine and/or fecal insult i.e. the diaper wearer or a toilet seat.

To facilitate for the caregiver, the method may compare each registered characteristic with the predetermined characteristic in the receiver unit; and present visual or aural information in the receiving unit so as to indicate whether urine and/or feces have been detected. Thereby, the caregiver can easily receive information regarding incidents and decide whether diapers need to be changed or not.

The receiver unit may also receive information from several sensor units, i.e. sensor units worn by several bed-bound patients in a hospital ward or several sensor units placed in a toilet cubicle. Thereby, the user can receive information regarding several sensor units at once by the receiver unit, and in the case of incontinence, a caregiver can receive information on several patients simultaneously.

The information may also be forwarded to a remote server unit. The remote server unit may be placed in a staffroom or in a corridor such that a user of the system does not have to be in the room of the diaper wearer when evaluating if the diaper need changing. The system may also be used in a public washroom such that the user may determine before entering the washroom if a toilet has been used and thus need thorough cleaning.

The principles can be implemented in larger networks including different facilities, for example several hospitals or hotels or similar sites. In such case, a number of rooms or departments can be connected in a network, for example in the form of a wireless data communication network, in order to allow detection of urinal and fecal insults and for transmitting related information to one or more remote, central servers. Such communication may allow, for example, planning of staff and cleaning operations in an efficient and centralized manner.

The time of the incident may also be registered and determined based on the detection of gas components indicative of feces and/or urine. Thereby, information regarding when the incident happened may be monitored, and the time which has passed since the incident occurred may also affect the frequency at which a soiled diaper should be changed.

Also disclosed is a system for detecting urine and feces, including a sensor unit including at least one gas sensor for detecting the concentration of a gas component indicative of urine and at least one gas sensor for detecting the concentration of a gas component indicative of feces and a receiving unit connectable to the sensor and arranged for providing an indication of any presence or urine and/or feces based on information from the sensors.

The receiving unit is arranged for registering, based on the detected concentration for each gas component, a characteristic corresponding to the variation over time of the concentration of the gas component, and comparing the characteristic with a predetermined characteristic indicative of urine and feces, respectively. Thereby, the presence of urine and/or feces may be detected with high accuracy and reliability.

The receiving unit may include an indicator for providing visual or aural information as to whether urine and/or feces have been detected. Thereby, the user, such as a care giver or a cleaner, may easily detect that an incident has occurred. The user may also easily distinguish between a urinal and a fecal insult by monitoring the receiver unit, and must not rely on manual detection by smell or visual inspection. The receiving unit may be a mobile unit such as a mobile telephone, a tablet computer or similar.

The system may further include a remote server unit connectable to the receiving unit and for storing information from the gas sensors. Thus, information may be gathered and compiled over time, and statistics may be generated. Thereby, it may be easier to predict when an incident by a patient wearing a sanitary article may occur, or deciding how often a toilet must be cleaned based on statistics of how often urinal vs fecal incidents occur. Such statistics could help personnel in planning their work. It may also help calculate the number of staff needed at different times or at different locations.

According to an embodiment, the system can be used for detecting feces only, including a sensor unit including at least two gas sensors for detecting the concentration of a at least two gas components indicative of feces and a receiving unit connectable to the sensor and arranged for providing an indication of any presence of feces based on information from said sensors. In such a system, the receiving unit is arranged for registering, based on the information and for each gas component, a characteristic corresponding to the variation over time of the concentration of the gas component, and comparing the characteristic with a predetermined characteristic indicative of feces, respectively. The system provides an improved detection of the presence of feces over systems wherein only one gas sensor is used or wherein the presence is based on the registered concentration exceeding a threshold value instead of complying with a predetermined characteristic. The characteristic of the concentration, as it varies with time, is a better indication of the specific gas originating from a fecal source than just a momentary concentration exceeding a threshold.

BRIEF DESCRIPTION OF DRAWINGS

Embodiments of the invention will be described below with reference to an embodiment and the appended drawings, in which.

DETAILED DESCRIPTION OF EMBODIMENTS

Figure 1:
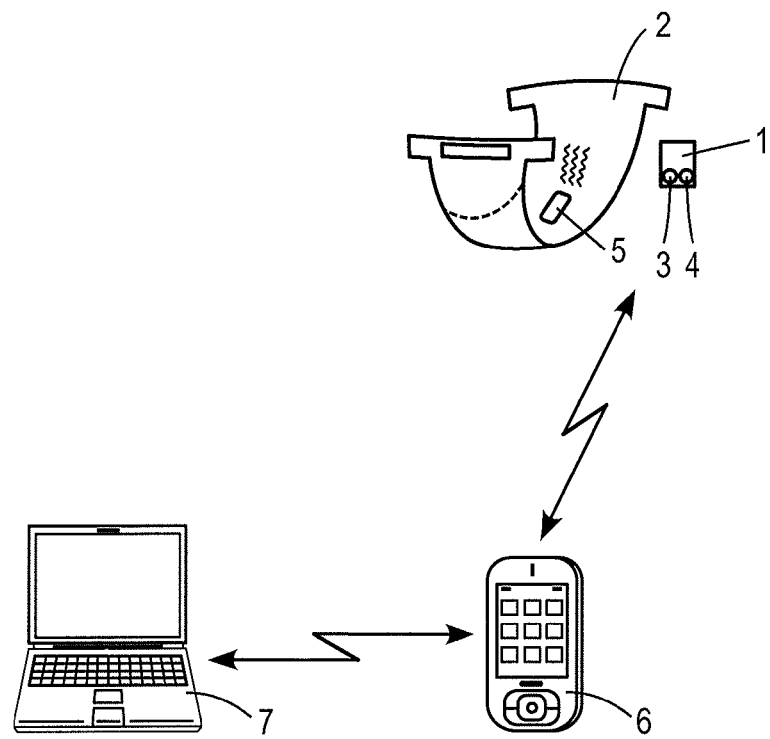
FIG. 1 shows a schematic view of a system according to an embodiment of the invention.

FIG. 1 shows one embodiment of the present invention. A sensor unit 1 is arranged in association with a sanitary article 2, such as an absorbent article such as a diaper in FIG. 1. In a certain embodiment, the sensor unit 1 is arranged on the side of a bed in which an incontinent wearer, i.e. a user of the sanitary product 2, is confined. Alternatively, the sensor unit 1 could be worn by the user in a belt around the waist, in a pocket, or in some other suitable manner provided that the sensor unit 1 is positioned in the close vicinity of the user's body.

The sensor unit 1 includes a first gas sensor 3 for detecting a gas component indicative of feces and a second gas sensor 4 for detecting a gas component indicative of urine. Alternatively, the sensor unit 1 may be provided with two or more gas sensors for detecting gas components indicative of feces, and/or two gas sensors for detecting gas components indicative of urine. In this manner, the sensor unit 1 can detect the components of the gas emitted from an insult 5 in the diaper 2, independently of whether it is a urinal or fecal insult 5. The sensor unit 1 is connected to a receiver unit 6, such as a mobile unit such as a mobile phone, a tablet computer, a PDA, a laptop computer or similar.

The connection between the sensor unit 1 and the receiver unit 4 can be wireless, and can be based on suitable wireless technology such as Bluetooth or Zigbee. Such nearfield communication technologies are well-known to the skilled person, and for this reason they are not described in detail here.

The receiver unit 6 receives data from the sensor unit 1 regarding the concentration of the gas component indicative of urine and the gas component indicative of feces, and registers a characteristic corresponding to each respective concentration over time. According to an embodiment, a "characteristic" should be regarded as a series of gas concentration values sampled at a corresponding number of points in time, i.e. a pattern of concentration values, which form a set of distinguishing features of the concentration of gas. According to an embodiment, these distinguishing features are in the form of curves or patterns, as indicated in FIG. 2.

The registered characteristics are compared to predetermined characteristics indicative of urine or feces, respectively. The mobile unit 6 includes an indicator for providing visual information to the user as to whether a urinal and/or fecal insult 5 have been detected in the sanitary article 2. Thus, the user of the receiver unit 6, who in many cases is a caregiver, a nurse or similar, may decide if it is suitable to change the sanitary article 2 or not.

The receiver unit 6 is further connected to a remote server unit 7. The receiver unit 6 is arranged for transmitting received data from the sensor unit 1 further on to the remote server unit 7. The remote server unit 7 could be arranged in a staff room or corridor, such that the information from the receiver unit 6 is available and stored at a central location. Based on the measurements of the sensor unit 1, the user of the receiver 6, e.g. a caregiver, may thus be notified that a fecal incident 5 has occurred in a specific location (i.e. where the sensor unit 1 is located), and go there to change the sanitary article 2. The remote server unit 7 also stores information over time, such that statistics of urinal and/or fecal incidents 5 are saved.

Figure 2:
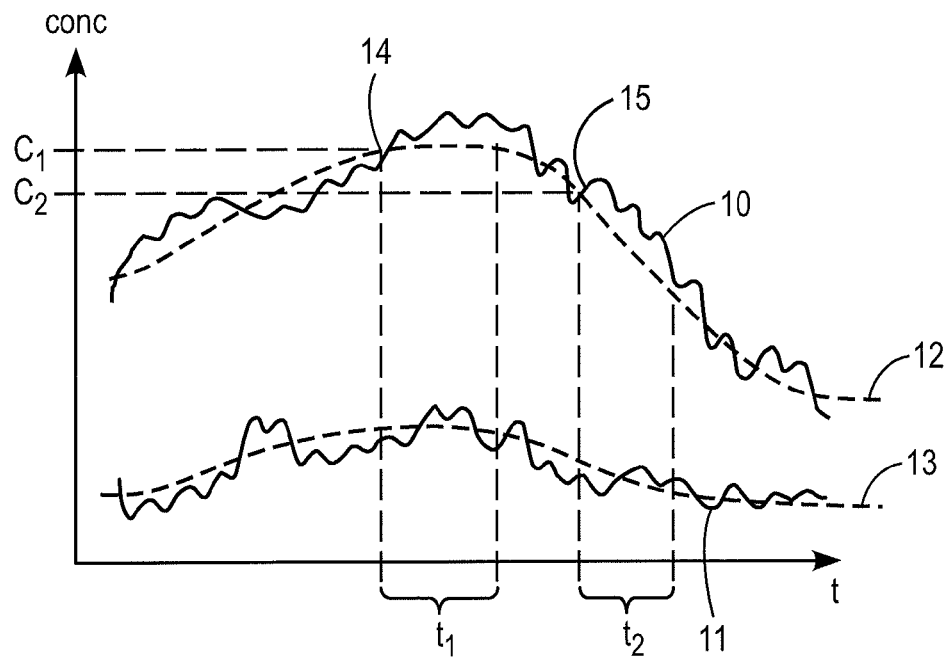
FIG. 2 shows a schematic view of two registered characteristics and two predetermined characteristics, as used in accordance with an embodiment of the method.

FIG. 2 shows one example of measurement by an embodiment of the invention in which two registered characteristics 10, 11 are shown as registered by the sensor unit 1. These registered characteristics 10, 11 will be described in detail below. In FIG. 2, the registered characteristics 10, 11 are indicated as solid lines, whereas corresponding predetermined, or "expected" characteristics 12, 13, which are intended to be compared with the registered characteristics 10, 11 are shown in the form of broken lines.

In this example, the sensor unit 1 is provided with two gas sensors 3, 4 for gas components indicative of feces; hydrogen gas ($H_2$) and hydrogen sulfide gas ($H_2S$). In FIG. 2, the registered characteristic 10 corresponds to the measured concentration of hydrogen gas component over time, and the registered characteristic 11 corresponds to the measured concentration of hydrogen sulfide gas component over time.

Other gas components, indicative of either urine or feces, may be illustrated in a similar way.

FIG. 2 also shows the predetermined characteristics 12, 13 corresponding to an expected characteristic resulting from the two gas components indicative of feces. The registered characteristics 10, 11 are compared to the predetermined characteristics 12, 13 as indicated schematically in FIG. 2. This comparison can be carried out in the receiver unit 6. If the registered characteristics 10, 11 conform generally to the predetermined characteristics 12, 13 then the presence of feces is indicated by means of the receiving unit 4.

In the example illustrated in FIG. 2, an indication of the presence of feces will be given if the registered characteristic 10 conforms to the predetermined characteristic 11, which can be confirmed by determining if the concentration of the gas component of the registered characteristic 10 exceeds a predetermined first value $c_1$, which is indicated by means of reference numeral 14 along the predetermined characteristic 12, and remains higher than said threshold value $c_1$ during a first predetermined period of time $t_1$. An indication of a presence of feces may correspond to this single comparison, i.e. by determining whether the concentration exceeds the threshold value $c_1$ during the first time period $t_1$. In order to provide a more accurate process for determining the presence of feces, a further comparison can be made; if the concentration of the gas component of the registered characteristic 10 exceeds a predetermined second value $c_2$ (as indicated by reference numeral 15) during a second predetermined period of time $t_2$, this is also interpreted as an indication of the presence of feces. If both concentration values $c_1$, $c_2$ are exceeded during the corresponding time periods $t_1$, $t_2$, the registered characteristic 10 is regarded as being in conformity with the predetermined characteristic 11.

Further measurements and comparisons of whether predetermined concentration values exist during predetermined time periods can be used in order to provide an even more accurate method for indicating the presence of feces.

The predetermined characteristic may be based on a standard concentration curve which has been measured and determined for a specific gas based on repeated tests following a specific type of incident, or any other suitable way of predetermining the pattern.

Each gas indicative of either urine or feces has an individual concentration distribution curve, i.e. a characteristic following a urine or fecal incident. The gas may be present at a high concentration to start with and then rapidly dissolve into the atmosphere, i.e. the decline of concentration is rapid. This is the case of e.g. the volatile gas of hydrogen following a fecal incident. Other gases may be present at a relatively low level over the same period of time following the incident, i.e. the decline of the gas concentration is slow. This is the case of heavy organic gases and hydrogen sulfide following a fecal incident. The concentration curves following an incident are thus indicative of each gas. By registering the characteristic over time of the concentration of a specific gas, and comparing the characteristic with an expected, predetermined characteristic, it is possible to determine the presence of the gas and thus confirm the presence of an incident.

An accurate determination of the presence of an incident may help in determining when a diaper should be changed, thereby leading to better hygiene of individuals needing help changing their diaper. It may also assist in determining when a toilet needs to be thoroughly cleaned.

The pattern of a gas concentration may be referred to as a tag. Hence, there could be separate feces tags and urine tags. In this manner, the system can be used for distinguishing between insults due to urine and feces, respectively.

With reference to FIG. 2, it can be noted that the actual values of the threshold values $c_1$, $c_2$ and the time periods $t_1$, $t_2$ can be predetermined depending on for example the accuracy of the gas sensors and the expected gas concentration in the location where the fecal and urinal insults can be expected to occur.

The principles shown in FIG. 2 regarding the detecting of feces can be applied in a similar fashion for measuring one or more gas components indicative of urine.

In another example, also illustrated in FIG. 2, an indication of presence of feces will be given if the registered characteristic 10 conforms to the predetermined characteristic 11 in a manner so that the derivate of the registered characteristic 10 at a predetermined point in time conforms to a predetermined, or "expected" derivate of the predetermined characteristic 12 at the corresponding point in time. Thereby, the determination is independent of the level of concentration of gas component, and only dependant on how the concentration varies—i.e. increases or decreases—over time. Thus, the gas source may be identified as a fecal insult 5 and may be easily differentiated from other gas components sources such as release of intestinal gas during passing of gas, which correspond to a different pattern of concentration over time following the release.

An example of suitable gases are the non-volatile hydrogen sulfide gas and the volatile hydrogen gas. These have different characteristics and if both these characteristics are detected, then the presence of feces may be indicated with high accuracy. Thereby, the accuracy of the method is higher than basing the presence of feces on the detection of only one gas indicative of feces. The presence of two gases in combination also rules out the possibility that the gas is detected on the basis of a gas leak, a nearby diaper wearer, toilet etc.

The two alternative requirements of determining if the registered characteristic conforms to the predetermined characteristic as exemplified above may be combined. Hence, determination of conformity between the registered characteristic and the predetermined characteristic may be based on both threshold values and the derivates at predetermined periods of time. By combining the two requirements of conformity, the accuracy and reliability of the method is increased because the method depends both on the concentration level of the gas components as well as the variation in concentration over time.

The two registered characteristics 10, 11 may also be combined into a combined characteristic after being separately registered. The characteristics may be combined by adding the concentration values of each gas component for each point in time where measurements are taken. The combined registered characteristic is subsequently compared to a combined predetermined characteristic in order to determine if presence of feces should be indicated based on the conformity of the registered combined characteristic and the preregistered combined characteristic. One way of combining the gas concentration values is to detect a concentration of a first gas (for example hydrogen) and to detect a concentration of a second gas (for example hydrogen sulfide) at a particular point in time. If the ratio of these two concentration values corresponds generally to an expected ratio (which corresponds to the presence of feces), this will be regarded as corresponding to a fecal insult.

The concentration values of each one of the two registered characteristics 10, 11 may also be assigned a weight value before combining them into one combined characteristic. Thereby, one concentration of gas component can be set to be more important in the detection, hence given a higher weight value.

The invention is not limited to the above-mentioned embodiments, but can be varied within the scope of the claims. For example, detection of urinal and/or fecal incontinence can be carried out by embodiments of the invention even though a person on which the insult occurs is not wearing any sanitary article.

Furthermore, the comparison between the registered characteristic and the predetermined characteristics can be carried out in the receiver unit, alternatively in the sensor unit.

Also, other parameters than the gas concentrations as described above can be used in order to determine whether fecal or urine insults have occurred. For example, the environmental temperature can be used in this regard, since it can be expected that the temperature close to the location of the insult has different values depending on the type of insult. Also, the air humidity can be used in a similar manner, since it can be expected that the humidity close to the location of the insult has different values depending on the type of insult.

The invention claimed is:

1. A method of detecting urine and feces comprising:
   detecting the concentration of a gas component indicative of urine and the concentration of a gas component indicative of feces by:
   registering, for each detected gas component, a characteristic corresponding to variation over time of the concentration of each detected gas component;
   determining whether each registered characteristic conforms to a predetermined characteristic corresponding to variation over time of a concentration of a corresponding gas component, wherein the predetermined characteristic is independent of the concentration of the detected gas component and the determination is dependent upon how the concentration of the detected gas component varies over time;
   indicating a presence of urine if the registered characteristic of the detected gas component indicative of urine generally conforms with the predetermined characteristic of the corresponding gas component; and
   indicating a presence of feces if the registered characteristic of at least one gas component indicative of feces generally conforms to the predetermined characteristic of the same gas component.

2. The method of detecting urine and feces according to claim 1, wherein the indication of any presence of urine and feces, respectively, comprises determining whether the concentration of any of said gas components exceeds at least one predetermined limit value during a predetermined period of time.

3. The method of detecting urine and feces according to claim 1, wherein the indication of any presence of urine and feces, respectively, comprises determining whether a derivative of the registered characteristic during a predetermined period of time generally conforms to a corresponding expected derivative of the predetermined characteristic.

4. The method of detecting urine and feces according to claim 1, wherein the method further comprises:
   detecting the concentration of at least two gas components indicative of feces;
   for each detected gas component indicative of feces, registering a separate characteristic corresponding to the variation over time of the detected gas component concentration;
   combining the registered separate characteristics;
   comparing a combination of the registered characteristics with a predetermined combination of characteristics; and
   indicating a presence of urine and/or feces if the combined registered characteristics generally conforms with the predetermined combined characteristics.

5. The method of detecting urine and feces according to claim 4, wherein the method further comprises:
   assigning a weight value for each of said separate registered characteristics before combining the characteristics.

6. The method of detecting urine and feces according to claim 1, wherein the detected gas component indicative of feces is chosen from a group consisting of hydrogen gas, hydrogen sulfide, and an organic compound gas.

7. The method of detecting urine and feces according to claim 1, wherein the detected gas component indicative of urine is ammonia gas.

8. The method of detecting urine and feces according to claim 1, wherein the method further comprises:
   providing a sensor unit, comprising gas sensors for detecting each of said gas components, and
   transmitting information regarding detection of said gas components from said sensor unit to a receiver unit.

9. The method of detecting urine and feces according to claim 8, wherein the method further comprises:
   presenting visual or aural information in said receiving unit as to whether urine and/or feces have been detected.

10. The method of detecting urine and feces according to claim 8, wherein the method further comprises forwarding said information to a remote server unit.

11. The method of detecting urine and feces according to claim 8, wherein the method further comprises:
    arranging said sensor unit in a close vicinity of a sanitary product or a wearer of said sanitary product.

12. A system for detecting urine and feces, comprising:
    a sensor unit comprising a gas sensor for detecting the concentration of a gas component indicative of urine and a gas sensor for detecting the concentration of a gas component indicative of feces; and
    a receiving unit connectable to the sensor unit, and;
    wherein said receiving unit is arranged for registering based on said detected concentration for each gas component, a characteristic corresponding to variation over time of the concentration of each detected gas component, and determining whether each registered characteristic conforms to a predetermined characteristic corresponding to variation over time of a concentration of a corresponding gas component, wherein the predetermined characteristic is independent of the concentration of the detected gas component and the determination is dependent upon how the concentration of the detected gas component varies over time, and wherein the receiving unit is arranged for providing an indication of any presence or urine and/or feces based on information from said gas sensors if the registered characteristic of said gas component indicative of urine/feces generally conforms to the predetermined characteristic of the same gas component, and the registered characteristic is determined to conform to the predetermined characteristic if the registered characteristic follows the variation over time of the predetermined characteristic.

13. The system for detecting urine and feces according to claim 12, wherein the receiving unit comprises an indicator for providing visual or aural information as to whether urine and/or feces have been detected.

14. The system for detecting urine and feces according to claim 12, wherein said receiving unit is a mobile unit.

15. The system for detecting urine and feces according to claim 12, wherein the system further comprises a remote server unit connectable to said receiving unit and for storing information from said gas sensors.

\* \* \* \* \*